(12) United States Patent
Stobie et al.

(10) Patent No.: US 6,333,326 B1
(45) Date of Patent: Dec. 25, 2001

(54) QUINOXALINEDIONES

(75) Inventors: Alan Stobie; Elisabeth Colette Louise Gautier; David Charles Waite; Robert James Crook, all of Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/367,303

(22) PCT Filed: Feb. 24, 1998

(86) PCT No.: PCT/EP98/01275

§ 371 Date: Aug. 2, 1999

§ 102(e) Date: Aug. 2, 1999

(87) PCT Pub. No.: WO98/38186

PCT Pub. Date: Sep. 3, 1998

(30) Foreign Application Priority Data

Feb. 27, 1997 (WO) .................................... PCT/EP97/00995
Jul. 25, 1997 (GB) .................................... 9715783

(51) Int. Cl.⁷ ....................... C07D 401/14; A61K 31/498
(52) U.S. Cl. ............................................. 514/249; 544/354
(58) Field of Search .............................. 544/354; 514/249

(56) References Cited

U.S. PATENT DOCUMENTS 5,283,244 * 2/1994 Sakamoto et al. .................... 514/249
5,285,244   2/1994 Bujese ................................. 355/256

FOREIGN PATENT DOCUMENTS 556 393  *  8/1993  (EP) .
9732873  12/1997  (WO) .

OTHER PUBLICATIONS

Lipton, *TINS*, vol. 16, pp. 527–532, 1993.*
McBurney, *Neurobiology of Aging*, vol. 15, pp. 271–273, 1994*

* cited by examiner

*Primary Examiner*—Emily Bernhardt
(74) *Attorney, Agent, or Firm*—P. C. Richardson; P. H. Ginsburg; J. W. Appleman

(57) ABSTRACT

This invention relates to 2,3(1H,4H)-quinoxalinedione derivatives which are selective antagonists of N-methyl-D-aspartate receptors. More particularly, this invention relates to 5-triazolyl-2,3(1H,4H)-quinoxalinedione derivatives and to the preparation of, compositions containing, and the uses of, such derivatives. It also relates to a method for treating acute neurodegeneration disorders and chronic neurological disorders.

16 Claims, No Drawings

QUINOXALINEDIONES

CROSS REFERENCE TO RELATED APPLICATIONS

This present application is a 371 filing of a PCT application PCT/EP98/01275 filed Feb. 24, 1998 which claims priority from under 35 U.S.C. 119 PCT/EP97/00995 having an international filing date of Feb. 27, 1997 and UK Application No. 97157838 filed Jul. 27, 1997.

This invention relates to 2,3(1H,4H)-quinoxalinedione derivatives which are selective antagonists of N-methyl-D-aspartate receptors. More particularly, this invention relates to 5-triazolyl-2,3(1H,4H)-quinoxalinedione derivatives and to the preparation of, compositions containing, and the uses of, such derivatives.

L-Glutamic acid is an excitatory amino acid neurotransmitter whose physiological role in the brain involves interaction with four receptors, three of which are named after the selective agonists NMDA (N-methyl-D-aspartate), AMPA (2-amino-3-hydroxy-5-methyl-4-isoxazolepropionic acid) and kainate. The fourth receptor is termed the metabotropic receptor. In addition to a binding site for glutamic acid, the NMDA receptor possesses high affinity binding sites for dissociative anaesthetics (e.g. ketamine), polyamines (e.g. spermine), glycine and certain metal ions (e.g. $Mg^{2+}$, $Zn^{2+}$). Since the NMDA receptor has an absolute requirement to bind glycine for activation to occur, glycine antagonists can act as functional NMDA antagonists.

In the region of a cerebral infarct, anoxia, for example, causes abnormally high concentrations of glutamic acid to be released. This leads to an over-stimulation of NMDA receptors resulting in the degeneration and death of neurones. Thus, NMDA receptor antagonists, which have been shown to block the neurotoxic effects of glutamic acid in vitro and in vivo, may be useful in the treatment and/or prevention of any pathological condition in which NMDA receptor activation is thought to be important. Examples of such conditions include acute neurodegenerative disorders arising from events such as stroke, transient ischaemic attack, peri-operative ischaemia, global ischaemia (following cardiac arrest) and traumatic head injury to the brain or spinal cord. In addition, NMDA antagonists may be of use in treating certain chronic neurological disorders such as senile dementia, Parkinson's disease and Alzheimer's disease. They may also have utility in conditions in which peripheral nerve function has been impaired such as retinal and macular degeneration.

Furthermore, NMDA antagonists have been shown to possess anti-convulsant and anxiolytic activity and may therefore be used to treat epilepsy and anxiety. NMDA antagonists may also attenuate the effects of alcohol withdrawal from physically dependent animals (K. A. Grant et al., J. Pharm.Exp.Ther., 260, 1017 (1992)) and thus NMDA antagonists may be of use in the treatment of alcohol addiction and pain. NMDA antagonists may also be useful in the treatment of hearing disorders (e.g. tinnitus), migraine and psychiatric disorders.

EP-A-0572852 describes pyrrol-1-yl-substituted 2,3(1H, 4H)-quinoxalinedione derivatives useful for the treatment of neurodegenerative illnesses and neurotoxic disorders of the central nervous system.

EP-A-0556393 discloses, inter alia, imidazolyl- or triazolyl-substituted 2,3(1H,4H)-quinoxalinedione derivatives with glutamate receptor antagonising activity, particularly NMDA-glycine receptor and AMPA receptor antagonising activities. However, no 5-triazolyl-substituted compounds are specifically described therein.

International Patent Application Publication No. WO 97132873 discloses 5-heteroaryl-2,3-(1H,4H)-quinoxalinedione derivatives with NMDA receptor antagonist activity. Example 114 of that Application allegedly describes the preparation of (−)-6,7-dichloro-5-[3-methoxymethyl-5-(1-oxidopyridin-3-yl)4H-1,2,4-triazol-4-yl]-2,3(1H,4H)-quinoxalinedione. However, further analysis of the product of Example 114 shows the stated title compound to be bound to a stoichiometric quantity of silica (see Reference Example 1 herein). This silica complex has been shown to have different properties compared with, and to be distinct, analytically, from, the stated title compound. Example 114 of that Application therefore discloses the preparation of a different compound to the alleged title compound although the skilled person, realising that a silica complex had been obtained, could readily apply common knowledge to prepare the stated title compound therefrom.

The present compounds are potent antagonists of the NMDA (glycine site) receptor. In addition, they are highly selective antagonists for the NMDA (glycine site) receptor in comparison to the AMPA receptor to which they have little, if any, affinity.

The present invention provides a novel, substantially pure compound of the formula:

(I)

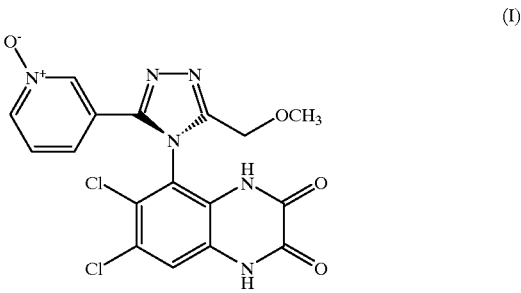

or a pharmaceutically acceptable salt or solvate thereof.

The expression "substantially pure" means the compound preferably is at least of 90% w/w purity, more preferably is at least of 95% w/w purity and most preferably is at least of 98% w/w purity. For the purpose of pharmaceutical applications, the compound would normally be manufactured to at least 99% w/w purity.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the calcium, lithium, magnesium, potassium, sodium, zinc, ethanolamine, diethanolamine and triethanolamine salts.

For a review on suitable salts see Berge et al, J.Pharm.Sci., 66, 1–19 (1977).

Suitable solvates include hydrates.

The compounds of the formula (I) are single stereoisomers known as atropisomers. Atropisomers are isomers that can be separated only because rotation about single bonds is prevented or greatly slowed (see "Advanced Organic Chemistry", Third Edition, Jerry March, John Wiley and Sons (1985)). They may be prepared conventionally from a corresponding optically pure intermediate or by resolution of a racemic mixture containing the opposite stereoisomer. This can be achieved by H.P.L.C. of the corresponding racemate using a suitable chiral support or by fractional crystallisation of the diastereoisomeric salts formed by reaction of the corresponding racemate with a suitable optically active acid or base.

The compounds of the formula (I) can be prepared by the following methods.

1) The compounds of the formula (I) can be prepared by acidic or basic hydrolysis of a compound of the formula:

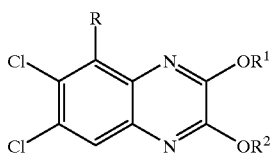

(II)

wherein R is group of the formula:

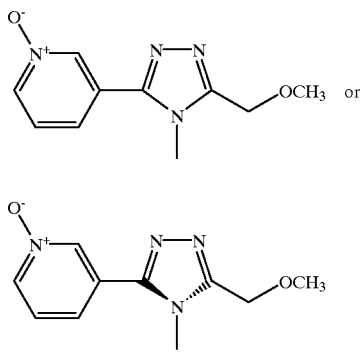

(III)

(IV)

and $R^1$ and $R^2$, either when taken alone or together, represent a group or groups that can be hydrolytically cleaved under acidic or basic conditions to provide a quinoxalinedione of the formula (I). Such group or groups are conventional and suitable examples will be well-known to the skilled person. Where R is a group of the formula (III), the reaction is followed by separation of the atropisomer of the formula (I) using conventional conditions.

Preferably $R^1$ and $R^2$ are either each independently selected from $C_1$–$C_4$ alkyl (preferably methyl or ethyl) and benzyl, optionally ring-substituted by from 1 to 3 substituents each independently selected from $C_1$–$C_4$ alkyl, $C_1$–$C_4$ alkoxy, halo, nitro and trifluoromethyl, or, when taken together, represent $C_1$–$C_6$ alkylene, CH(phenyl), CH(4-methoxyphenyl) or CH(3,4-dimethoxyphenyl).

Preferably, the reaction is carried out by acidic hydrolysis of a compound of the formula (II).

In a typical procedure, a compound of the formula (II) is treated with an aqueous solution of a suitable acid, e.g. a mineral acid such as hydrochloric acid, optionally in the presence of a suitable organic co-solvent, e.g. 1,4-dioxane. The reaction is usually carried out by heating the mixture at up to the reflux temperature of the solvent(s).

The intermediates of the formula (II) can be prepared by conventional methods, for example, a) by the route shown in Scheme I:

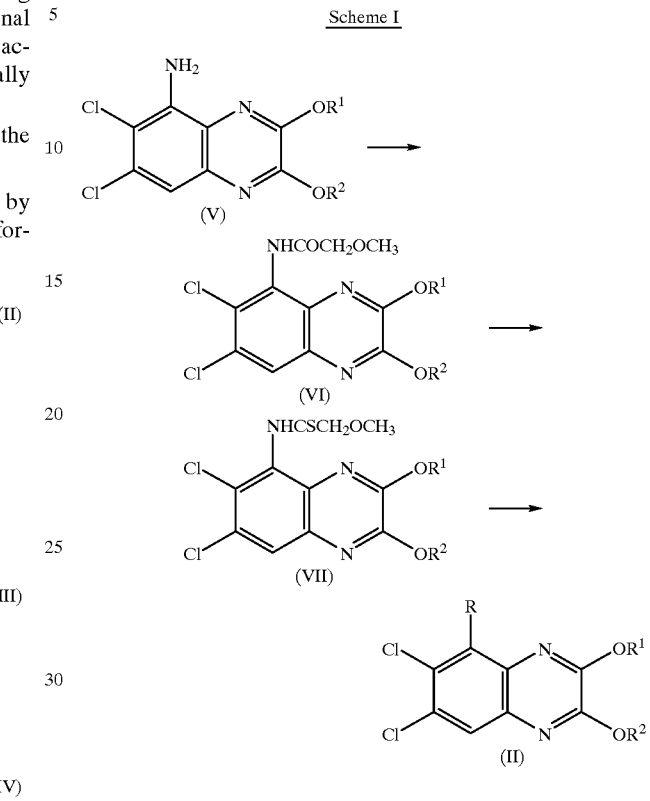

wherein R, $R^1$ and $R^2$ are as previously defined for a compound of the formula (II).

In a typical procedure, a 5-aminoquinoxaline of the formula (V) is reacted with a compound of the formula:

CH$_3$OCH$_2$COX$^1$ wherein $X^1$ is a suitable leaving group, e.g. chloro or bromo, in a suitable solvent, e.g. toluene or dichloromethane, and optionally in the presence of a suitable acid acceptor, e.g. pyridine, to provide an amide of the formula (VI).

An amide of the formula (VI) can be converted to a thioamide of the formula (VII) by treatment with 2,4-bis(4-methoxyphenyl)-1,3-dithia-2,4-diphosphetane-2,4-disulphide (Lawesson's reagent) in a suitable solvent, e.g. toluene or tetrahydrofuran.

A thioamide of the formula (VII) can be converted to a compound of the formula (II) by treatment with a compound of the formula:

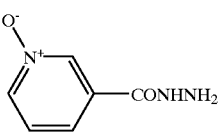

in the presence of mercury (II) oxide, optionally a desiccant, e.g. 4A molecular sieves, and a suitable solvent, e.g. n-butanol. A compound of the formula (II) where R is a group of the formula (III) may be resolved to provide a compound of the formula (II) where R is a group of the formula (IV) using conventional techniques, e.g. chiral H.P.L.C.; or b) by using a similar method to that shown in Scheme I to prepare the corresponding pyridine compound of the formula:

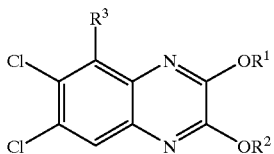
(VIII)

wherein R³ is a group of the formula:

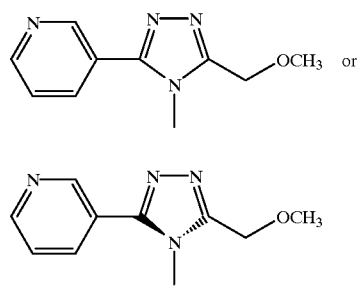
(IX)

(X)

and R¹ and R² are as previously defined for a compound of the formula (II), followed by N-oxidation thereof.

The N-oxidation can be performed using 3-chloroperoxybenzoic acid in a suitable solvent, e.g. aqueous methanol or acetone. Other suitable N-oxidation conditions include using hydrogen peroxide in acetic acid, dimethyldioxirane in acetone, monoperphthalic acid in acetic acid/methanol, OXONE (trade mark, potassium peroxymonosulphate) in a suitable solvent such as water, acetone or dichloromethane, and sodium perborate in acetic acid.

Again, a compound of the formula (II) where R is a group of the formula (III) may be resolved to provide a compound of the formula (II) where R is a group of the formula (IV) as described in method (a) above.

2) The compounds of the formula (I) can also be prepared by N-oxidation of a compound of the formula:

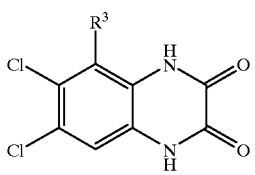
(XI)

where R³ is a group of the formula:

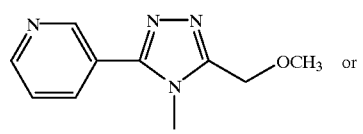
(IX)

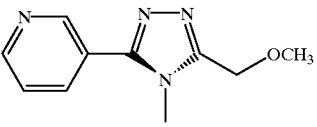
(X)

The N-oxidation can be carried out using a suitable oxidising agent, e.g. 3-chloroperoxybenzoic acid, and a suitable solvent, e.g. methanol or acetone. Other suitable N-oxidation conditions include using hydrogen peroxide in acetic acid, dimethyldioxirane in acetone, monoperphthalic acid in acetic acid/methanol, OXONE (trade mark, potassium peroxymonosulphate) in a suitable solvent such as water, acetone or dichloromethane, and sodium perborate in acetic acid.

Where R³ is a group of the formula (IX), the reaction is followed by separation of the atropisomer of the formula (I) using conventional conditions.

The compounds of the formula (XI) may be prepared by acidic or basic hydrolysis of the compounds of the formula (VIII) using the conditions described in Method (1).

3) A compound of the formula (I) can be prepared from its corresponding silica complex by treating a solution of the complex in a suitable solvent, e.g. methanol, with a suitable acid, e.g. a mineral acid (e.g. hydrochloric acid) or acetic acid. This acid treatment degrades the silica complex and liberates a compound of the formula (1).

During the preparation of a compound of the formula (I), the compound must not be treated with silica (e.g. during chromatography) otherwise it will become bound with a stoichiometric quantity thereof to form a different compound, i.e. a silica complex of the required compound. Accordingly, a compound of the formula (I) is preferably purified by reverse phase gel chromatography.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The binding affinity of compound of the formula (I) for the glycine site of the NMDA receptor may be measured by testing its ability to displace a selective glycine site radioligand from rat brain membranes as described in Brit. J. Pharm., 104, 74 (1991). In a variation of this method, thoroughly washed membrane protein is incubated with [³H]-L-689,560 (Mol. Pharmacol., 41, 923 (1992)) for 90 minutes using tris-acetate buffer (pH 7.4). Displacement of the radioligand, using a range of test compound concentrations, is used to derive $IC_{50}$ (50% inhibitory concentration) values.

Functional in vitro glycine antagonism is demonstrated by the ability of the compounds to inhibit the depolarisations in rat cortical slices induced by NMDA by a similar method to that described in J. Med. Chem., 33, 789 (1990) and Brit. J. Pharm., 84, 381 (1985). In a variation of the procedure, the response to a standard concentration of NMDA is measured in the presence of a range of test compound concentrations and the results obtained are used to derive $EC_{50}$ (50% effective concentration) values.

The binding affinity of the compounds of the invention for the AMPA receptor may be measured by testing their ability to displace the radioligand [$^3$H]-AMPA from rat brain membranes. Membrane homogenate is incubated with radioligand (10 nM) in the presence or absence of test compounds at various concentrations at 4° C. for 45 minutes. Free and bound radiolabel are separated by rapid filtration and radioactivity is measured by liquid scintillation counting.

The compounds of the formula (I) can be administered to a subject to be treated alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The compounds have potential for absorption through the gastrointestinal tract and thus administration by slow release formulations is also possible.

In general, a therapeutically effective daily oral dose of the compounds of formula (I) is likely to range from 0.1 to 100 mg/kg body weight of the subject to be treated, preferably 1 to 20 mg/kg, and an intravenous or subcutaneous daily dose is likely to range from 0.01–20 mg/kg body weight of subject to be treated, preferably 0.1–20 mg/kg. The compounds of the formula (I) may also be administered by intravenous infusion at a dose which is likely to range from 0.01–10 mg/kg/hr.

Tablets or capsules of the compounds may be administered singly or two or more at a time, as appropriate.

The physician will determine the actual dosage which will be most suitable for an individual patient and it will vary with the age, weight and response of the particular patient. The above dosages are exemplary of the average case. There can, of course, be individual instances where higher or lower dosage ranges are merited and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

It is to be appreciated that reference to treatment includes prophylaxis as well as the alleviation of established symptoms of the disease.

Thus the invention further provides:
i) a pharmaceutical composition comprising a compound of the formula (I), or a pharmaceutically acceptable salt or solvate thereof, together with a pharmaceutically acceptable diluent or carrier;

ii) a compound of the formula (I), or a pharmaceutically acceptable salt, solvate or composition thereof, for use as a medicament;

iii) the use of a compound of the formula (I), or of a pharmaceutically acceptable salt, solvate or composition thereof, for the manufacture of a medicament for the treatment of a disease by producing an antagonist effect at a NMDA receptor;

iv) use as in (iii) where the disease is an acute neurodegenerative or a chronic neurological disorder;

v) a method of treatment of a mammal to treat a disease by producing an antagonist effect at a NMDA receptor, which comprises treating said mammal with an effective amount of a compound of the formula (I) or with a pharmaceutically acceptable salt, solvate or composition thereof;

vi) a method as in (v) where the disease is an acute neurodegenerative or a chronic neurological disorder;

vii) a compound of the formula (II) where R is a group of the formula (III) or (IV); and viii) a compound of the formula (VIII) where $R^3$ is a group of the formula (X).

The following Examples illustrate the preparation of the compounds of the formula (I) and a composition thereof.

Melting points were determined using a Buchi apparatus in glass capillary tubes and are uncorrected. Low Resolution Mass Spectroscopic (LRMS) data were recorded on a Fisons Trio 1000 Mass Spectrometer (thermospray using ammonium acetate in aqueous methanol as the carrier or atmospheric pressure chemical ionisation (APCI) using 97.5:2.5, by volume, methanol:acetic acid and gaseous nitrogen as the carrier). NMR data were recorded on a Varian Unity 300 or a Varian Inova 400 NMR instrument (300 and 400 MHz, respectively) and were consistent with the assigned structures. Proton NMR shifts are quoted in parts per million downfield from tetramethylsilane. The purity of the compounds was carefully assessed using analytical TLC and proton NMR and the latter technique was used to calculate the amount of solvent present in solvated samples. The term "residue" used in the microanalysis data indicates the residual material remaining following combustion, i.e. the non-flammable material.

EXAMPLE 1

(−)-6,7-Dichloro-5-[3-methoxymethyl-5-(1-oxidopyridin-3-yl)-4H-1,2,4-triazol-4-yl]-2.3(1H,4H)-quinoxalinedione hydrate

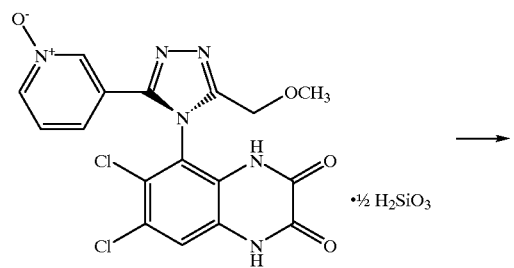

9

-continued

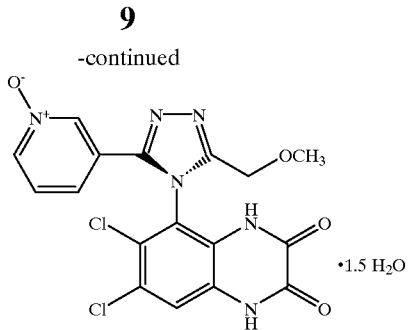

·1.5 H₂O

Concentrated hydrochloric acid (1 ml) was added to a stirred solution of (−)-6,7-dichloro-5-[3-methoxymethyl-5-(1-oxidopyridin-3-yl)-4H-1,2,4-triazol-4-yl]-2,3(1H,4H)-quinoxalinedione, silica complex (See Reference Example 1) (2.3 g, 4.64 mmol) in methanol (40 ml) and the mixture stirred for 2 hours. The solid precipitate was collected by filtration to afford the title compound as a white solid (1.4 g, 65%). mp 264–265° C.

Found: C, 44.34; H, 3.21; N, 18.14; residue, 0.00. $C_{17}H_{12}Cl_2N_6O_4$. 1.5 $H_2O$ requires C, 44.17; H, 3.21; N, 18.18; residue 0.00%. $^1$H-NMR (300 MHz, $d_6$-DMSO): δ=3.12 (3H, s), 4.36 (2H, m), 7.18 (1H, d, J=9.5 Hz), 7.36 (1H, dd, $J_1=J_2=9.5$ Hz), 7.42 (1H, s), 8.24 (1H, d, J=9.5 Hz), 8.30 (1H, s), 12.22 (1H, s), 12.24 (1H, s). m/z (thermospray): 435 (MH$^+$). $[\alpha]_D^{25}$ −235° (c=0.1, water).

EXAMPLE 2

(−)-67-Dichloro-5-[3-methoxymethyl-5-(1-oxidopyridin-3-yl)-4H-1,2,4-triazol-4-yl]-2.3(1H,4H)=quinoxalinedione hydrate

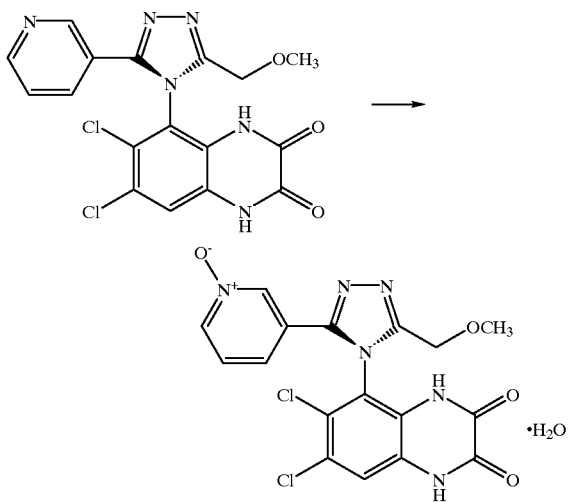

·H₂O

A solution of 3-chloroperoxybenzoic acid (50–55% w/w in water containing 3-chlorobenzoic acid impurity, 16.1 g, 47 mmol) was added to a solution of (−)-6,7-dichloro-5-[3-methoxymethyl-5-(3-pyridyl)-4H-1,2,4-triazol-4-yl]-2,3(1H,4H)-quinoxalinedione (see Preparation 1) (13.8 g, 31 mmol) in methanol (400 ml) at room temperature. The reaction mixture was stirred at room temperature for 3.5 days. The reaction mixture was preabsorbed on reverse phase gel (MCI Gel CHP20P [trade mark], 75–100 μ) and purified by chromatography on reverse phase gel (MCI Gel CHP20P [trade mark], 75–100

10

μ) by gradient elution using water:methanol (3:1 changing to 2:1, by volume) as the eluent to give, after combination and concentration of the appropriate fractions, a light yellow solid which was recrystallised from methanol to give the title compound (7.6 g, 54%) as a colourless solid. mp 265–267° C.

Found: C, 45.01; H, 3.08; N, 18.65. $C_{17}H_{12}Cl_2N_6O_4.H_2O$ requires C, 45.05; H, 3.11; N, 18.54%. $^1$H-NMR (300 MHz, $d_6$-DMSO): Identical spectrum to that obtained for the compound of Example 1. m/z (thermospray): 435 (MH$^+$); $[\alpha]_D^{25}$ −224° (c=0.1, water).

EXAMPLE 3

(−)-6,7-Dichloro-5-[3-methoxymethyl-5-(1-oxidopyridin-3-yl)-4H-1,2,4-triazol-4-yl]-2,3(1H, 4H)-quinoxalinedione (−)-6,7-Dichloro-5-[3-methoxymethyl-5-(3-pyridyl)-4H-1,2,4-triazol-4-yl]-2,3(1H,4H)-quinoxalinedione (see Preparation 1) (412.2 g, 0.98 mol) and OXONE (trade mark) (1.44 kg, 2.3 mol) were slurried in water (4.13 L) and the mixture stirred at ambient temperature for 60 hours. Saturated aqueous sodium thiosulphate solution (2.2 L) was added and the slurry stirred for 1 hour before being filtered under reduced pressure. The filter cake was slurried at ambient temperature for 4 hours in 1:1, by volume, isopropyl alcohol: dichloromethane (111 L) and the solid collected by filtration. The filtrate was vaporated under reduced pressure to give the title compound as a colourless solid (366 g).

EXAMPLE 4

(−)-6,7-Dichloro-5-[3-methoxymethyl-5-(1-oxidopyridin-3-yl)-4H-1,2,4-triazol-4-yl]-2,3(1H, 4H)-quinoxalinedione, sodium salt, hydrate Sodium hydroxide (9.72 ml of a 1 molar aqueous solution, 9.72 mmol) was added to a stirred suspension of (−)-6,7-dichloro-5-[3-methoxymethyl-5-(1-oxidopyridin-3-yl)-4H-1,2,4-triazol-4-yl]-2,3(1H,4H)-quinoxalinedione hydrate (see Example 2) (4.406 g, 9.72 mmol) in water (60 ml) and the mixture stirred for Part (i) of the following Reference Example 1 is a repeat preparation of the compound of Example 114 of International Patent Application Publication no. WO 97/32873. In Part (ii), the product obtained was recrystallised from aqueous acetone.

REFERENCE EXAMPLE 1

(−)-6,7-Dichloro-5-[3-methoxymethyl-5-(1-oxidopynidin-3-yl)-4H-1,2,4-triazol-4-yl]-2,3(1H, 4H)-quinoxalinedione, silica complex

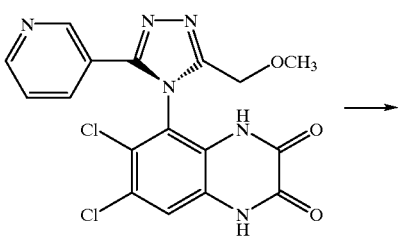

-continued

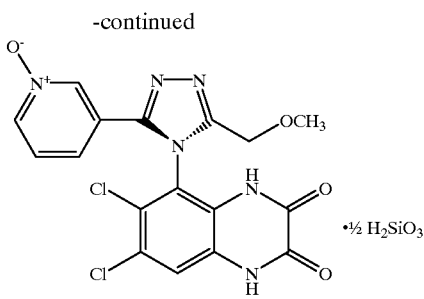

(i) A solution of 3-chloroperoxybenzoic acid (0.85 g, 4.93 mmol) in acetone (20 ml) was added in one portion to a suspension of (−)-6,7-dichloro-5-[3-methoxymethyl-5-(3-pyridyl)-4H-1,2,4-triazol-4-yl]-2,3(1H,4H)-quinoxalinedione (see Preparation 1) (1.0 g, 2.24 mmol) in acetone (40 ml) which caused all the solid to dissolve. The reaction was stirred at room temperature for 40 minutes after which time a white solid began to form. The reaction mixture was allowed to stir at room temperature for 3 days. The white solid was collected by filtration (this solid contained less than 90% w/w of the N-oxide product)[1] and subjected to flash chromatography on silica gel using dichloromethane:methanol:glacial acetic acid (90:10:1, by volume) as the eluant to give, after combination and concentration of the appropriate fractions, the title compound as a white solid, (0.16 g). m.p. >310° C.

$^1$H-NMR (300 MHz, $d_6$-DMSO): δ=1.90 (s, acetic acid 0.3 eq), 3.10 (3H, s), 4.32 (2H, m), 7.22 (1H, m), 7.40 (2H, m), 8.10 (1H, m), 8.22 (1H, m). 5 minutes. The resulting solution was filtered and the filtrate freeze-dried to give the title compound (4.5 g, 98%) as a pale yellow solid. mp 303° C. (decomp.). Found: C, 41.40; H, 3.05; N, 16.99. $C_{17}H_{11}Cl_2N_6NaO_4$. $2H_2O$ requires C, 41.40; H, 3.07; N, 17.04%. $^1$H-NMR (400 MHz, $d_6$-DMSO): δ=3.08 (3H, s), 4.24 (2H, m), 7.22 (2H, m), 7.38 (1H, dd, $J_1=J_2=9.5$ Hz), 8.02 (1H, s), 8.20 (1H, m), 11.66 (1H, s). $[α]_D^{25}$−277° (c=0.1, water).

EXAMPLE 5

Intravenous formulation of (−)-6,7-Dichloro-5-[3-methoxymethyl-5-(1-oxidopyridin-3-yl)-4H-1,2,4-triazol-4-yl]-2,3(1H,4H)-quinoxalinedione, sodium salt, hydrate A formulation suitable for administering a 20 mg/ml dose of the active component by intravenous injection was prepared using (−)-6,7-dichloro-5-[3-methoxymethyl-5-(1-oxidopyrdin-3-yl)-4H-1,2,4-triazol-4-yl]-2,3(1H,4H)-quinoxalinedione, sodium salt, $2H_2O$ (see Example 4) (22.7 mg per unit dose), sodium chloride (9.0 mg per unit dose) and water for injections (to 1.0 ml).

To prepare the formulation, sodium chloride is dissolved in 75% of the total volume of water in a suitable vessel with mixing. (−)-6,7-Dichloro-5-[3-methoxymethyl-5-(1-oxidopyridin-3-yl)-4H-1,2,4-triazol-4-yl]-2,3(1H,4H)-quinoxalinedione, sodium salt, $2H_2O$ is then added and dissolved by mixing. The solution is then made up to volume with water and filtered through a clarifying 0.2 micron filter. The filtrate is filled into sterile 10 ml glass ampoules under aseptic conditions using a terminal clarifying filter and the ampoules sealed.

m/z (thermospray): 435. $[α]_D^{25}$−235° (c=0.1, ethanol)*.
(*It should be noted that a clerical error occurred when stating the $[α]_D^{25}$ value in Example 114 of International Patent Application Publication no. WO 97132873. The stated "c=1.0" value is incorrect and this should have read "c=0.1").

(ii) Recrystallisation of this solid from aqueous acetone gave the title compound as a white solid. mp>310° C.

Found: C, 41.2; H, 3.1; N, 17.0; residue, 8.25. $C_{17}H_{12}Cl_2N_6O_4$. 0.5 $H_2SiO_3$. 1.2 $H_2O$ requires: C, 41.18; H, 3.13; N, 16.95; residue 7.87%. $^1$H-NMR (300 MHz, $d_6$-DMSO): δ=3.05 (3H, s), 4.37 (2H, m), 7.16 (1H, d, J=9.5 Hz), 7.32 (1H, s), 7.32 (1H, m), 7.98 (1H, s), 8.18 (1H d, J=9.5 Hz). $[α]_D^{25}$−199° (c=0.1, methanol).

Footnote

1. The method of Reference Example 1 (i) was repeated exactly and the precipitated white solid was collected by filtration (0.507 g).

This was found to contain 57.7% w/w (−)-6,7-dichloro-5-[3-methoxymethyl-5-(1-oxidopyrdin-3-yl)-4H-1,2,4-triazol-4-yl]-2,3(1H,4H)-quinoxalinedione when analysed by high pressure liquid chromatography (HPLC) using a 15 cm×0.46 cm i.d. Magellen (trade mark) C18 column and a gradient elution employing the following combinations of solvent A (acetonitrile) and solvent B (8.3 mM phosphate buffer adjusted to pH3.7 using phosphoric acid):

| Time (min.) | % (by volume) A | % (by volume) B | Duration (min.) |
|---|---|---|---|
|  | 2 | 98 | (Initial) |
| 0 | 98 | 2 | 30 |
| 35 | 2 | 98 | 1 |
| 45 |  |  | (Finish) | at a flow rate of 1 ml/min. and at ambient temperature.

The components of the eluted mixture were detected at a wavelength of 220 nm and samples of the compounds of Examples 4 and Preparation 1 and of 3-chloroperoxybenzoic acid were used as reference standards.

The following Preparations describe the manufacture of certain intermediates used in the preceding Examples and Reference Example.

PREPARATION 1

(±)-, (−)- and (+)-6,7-Dichloro-5-[3-methoxymethyl-5-(3-pyridyl)-4H-1,2,4-triazol-4-yl]-2,3(1H,4H)-quinoxalinedione

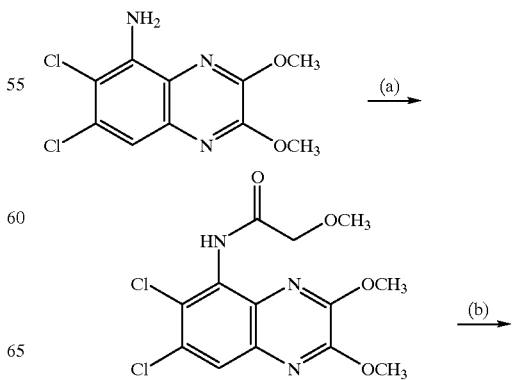

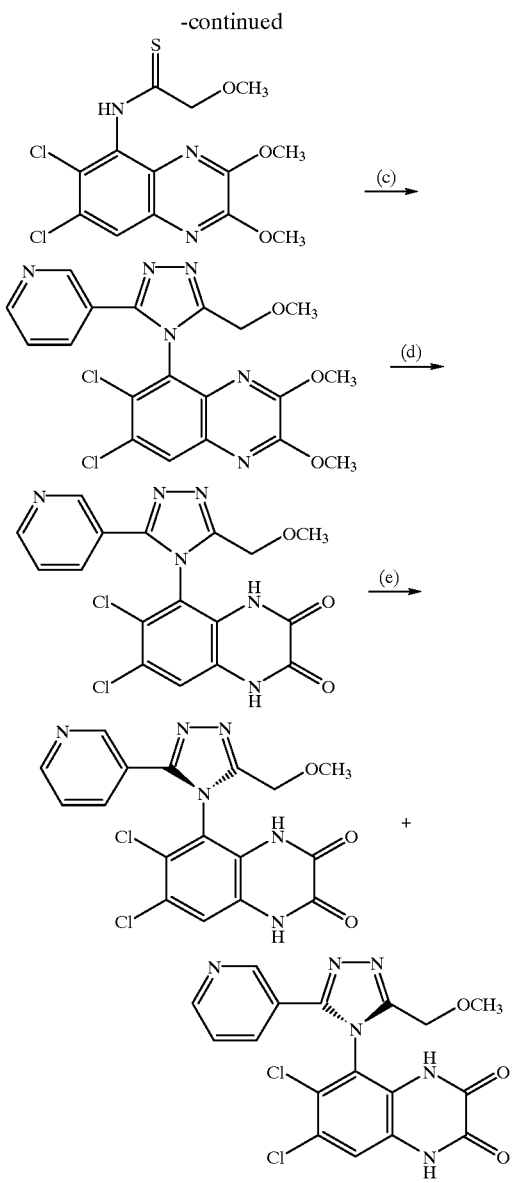

(a) Methoxyacetylchloride (27.3 ml, 32.4 g, 0.30 mol) was added to a stirred mixture of 5-amino-6,7-dichloro-2,3-dimethoxyquinoxaline (Preparation 2) (73.8 g, 0.27 mol) and pyridine (26.4 ml, 25.89, 0.33 mol) in dichloromethane (1.2 liters) at room temperature under nitrogen. After 18 hours standing at room temperature, the mixture was washed with 2M aqueous hydrochloric acid solution followed by brine, then dried (MgSO$_4$) and concentrated under reduced pressure. The residue was triturated with methanol and filtered to give 6,7-dichloro-2,3-dimethoxy-5-methoxyacetamidoquinoxaline (82.09, 88%) as an off-white solid. mp 171–173° C.

Found: C, 44.97; H, 3.75; N, 12.03. C$_{13}$H$_{13}$Cl$_2$N$_3$O$_4$ requires C, 45.11; H, 3.79; N, 12.14%.

(b) 2,4-Bis(4-methoxyphenyl)-1,3-dithia-2,4-diphosphetane-2,4-disulphide (Lawesson's reagent) (19.5 g, 48.2 mmol) was added to a solution of 6,7-dichloro-2,3-dimethoxy-5-methoxyacetamidoquinoxaline (27 g, 78 mmol) in tetrahydrofuran (480 ml) and the mixture was stirred for 18 hours at room temperature, then evaporated under reduced pressure. The residue was purified by flash chromatography on silica gel by gradient elution using hexane:dichloromethane (1:1 changing to 1:4, by volume) as the eluent to give 6,7-dichloro-2,3-dimethoxy-5-methoxythioacetamidoquinoxaline (29.1 g, >100%) as a white solid, mp 198–200° C., containing a minor impurity.

Found: C, 43.06; H, 3.65; N, 11.59. C$_{13}$H$_{13}$Cl$_2$N$_3$O$_3$S requires C, 43.11; H, 3.62; N, 11.60%.

c) A mixture of 6,7-dichloro-2,3-dimethoxy-5-methoxythioacetamido-quinoxaline (25.3 g, 69.9 mmol), nicotinic acid hydrazide (19.3 g, 140.8 mmol), mercury(II) oxide (15.1 g, 69.7 mmol) and 1,4-dioxane (600 ml) was heated under reflux for 18 hours. After cooling, the mixture was filtered through ARBOCEL (trade mark) filter aid and the residue washed with dichloromethane. The filtrate was concentrated under reduced pressure to afford a light brown solid which was partitioned between ethyl acetate and 2M aqueous hydrochloric acid solution. The layers were separated and the aqueous layer was extracted with dichloromethane (2×500 ml, 4×100 ml). The combined dichloromethane extracts were dried (MgSO$_4$) and concentrated under reduced pressure. The residue was crystallised from ethyl acetate/methanol to give (±)-6,7-dichloro-2,3-dimethoxy-5-[3-methoxymethyl-5-(3-pyridyl)-4H-1,2,4-triazol-4-yl)]quinoxaline (11.6 g, 37%) as a pale yellow solid. mp 189–191° C.

Found: C, 50.10; H, 3.57; N, 18.53. C$_{19}$H$_{16}$Cl$_2$N$_6$O$_3$·0.5H$_2$O requires: C, 50.01; H, 3.76; N, 18.42%.

(d) A mixture of (±)-6,7-dichloro-2,3-dimethoxy-5-[3-methoxymethyl-5-(3-pyridyl)-4H-1,2,4-triazol-4-yl] quinoxaline (3.0 g, 6.7 mmol), 2M aqueous hydrochloric acid solution (10 ml) and 1,4-dioxane (50 ml) was heated under reflux for 9 hours, cooled, and concentrated under reduced pressure. The residue was dissolved in 1M aqueous sodium hydroxide solution and acidified to pH 4.5 with concentrated hydrochloric acid to afford a thick white precipitate. This was collected by filtration and washed with water to give (±)-6,7-dichloro-5-[3-methoxymethyl-5-(3-pyridyl)-4H-1,2,4-triazol-4-yl]-2,3(1H,4H)-quinoxalinedione (2.0 g, 68%) as an off-white solid. mp 230–232° C.

Found: C, 46.23; H, 2.93; N, 19.00. C$_{17}$H$_{12}$Cl$_2$N$_6$O$_3$·1.25H$_2$O requires: C, 46.22; H, 3.31; N, 19.02%.

(i) (−)-N-Methylephedrine (0.88 g, 4.9 mmol) and then methanol (66 ml) were added to a stirred suspension of (±)-6,7-dichloro-5-[3-methoxymethyl-5-(3-pyridyl)-4H-1,2,4-triazol-4-yl]-2,3(1H,4H)-quinoxalinedione (1.9 g, 4.3 mmol) in ethyl acetate (400 ml) at room temperature. The mixture was heated to its boiling point. The mixture was filtered, the filtrate concentrated to three quarters of its volume and then cooled to room temperature. The solid obtained was collected by filtration and washed with ethyl acetate. The solid was crystallised from ethyl acetate/methanol to give a single diastereoisomer of the quinoxalinedione starting material as the (−)-N-methylephedrine salt (1.28 g, 43%). mp 162–164° C.

Found: C, 55.74; H, 5.38; N, 14.38. C$_{28}$H$_{29}$Cl$_2$N$_7$O$_4$·CH$_3$CO$_2$C$_2$H$_5$ requires: C, 55.98; H, 5.43; N, 14.28%. [α]$_D^{25}$−135° (c=0.1, ethanol).

(ii) A suspension of the (−)-N-methylephedrine salt (1.2 g, 1.7 mmol) from part (e)(i) in water (13 ml) at room temperature was acidified to pH 5 with concentrated hydrochloric acid and the suspension was stirred for 1 hour. The solid obtained was collected by filtration, washed with water and crystallised from water/ethanol to give (−)-6,7-dichloro-5-[3-methoxymethyl-5-(3-pyridyl)-4H-1,2,4-triazol-4-yl]-2,3(1H,4H)-quinoxalinedione (0.48 g, 62%) as a white solid. mp 220–222° C.

Found: C, 45.49; H, 3.21; N, 18.72. $C_{17}H_{12}Cl_2N_6O_3 \cdot 1.5H_2O$ requires C, 45.76; H, 3.39; N, 18.83%. $[\alpha]_D^{25} -214°$ (c=0.1, ethanol).

(iii) The combined filtrates from part (e)(i) were concentrated to dryness, the residue dissolved in water (20 ml), acidified to pH 3 with concentrated hydrochloric acid and the solid obtained was collected by filtration, washed with water and dried. (+)-N-Methylephedrine (0.37 g, 2.06 mmol) and then methanol (28 ml) were added to a stirred suspension of this solid (0.80 g, 1.87 mmol) in ethyl acetate (170 ml) at room temperature and the mixture was heated to its boiling point. The mixture was filtered, concentrated to three quarters of its volume and then cooled to room temperature. The solid obtained was collected by filtration and washed with ethyl acetate. The solid was crystallised from ethyl acetate/methanol to give a single diastereoisomer of the quinoxalinedione starting material as the (+)-N-methylephedrine salt (0.93 g, 32%) as a white solid. mp 165–167° C.

Found: C, 55.88; H, 5.40; N, 14.31. $C_{28}H_{29}Cl_2N_7O_4 \cdot 0.8 \, CH_3CO_2C_2H_5$ requires: C, 56.01; H, 5.33; N, 14.66%. $[\alpha]_D^{25} +127°$ (c=0.1, ethanol).

(iv) A suspension of the (+)-N-methylephedrine salt (0.90 g, 1.35 mmol) from part (e) (iii) in water (10 ml) at room temperature was acidified to pH 5 with concentrated hydrochloric acid and the suspension was stirred for 1 hour. The solid was collected by filtration and washed with water to give (+)-6,7-dichloro-5-[3-methoxymethyl-5-(3-pyridyl)-4H-1,2,4-triazol-4-yl]-2,3(1H,4H)-quinoxalinedione (0.41 g, 69%) as a white solid. mp 222–224° C.

Found: C, 46.44; H, 3.18; N, 19.01. $C_{17}H_{12}Cl_2N_6O_3 \cdot 1.25H_2O$ requires C, 46.22; H, 3.31; N, 19.02%. $[\alpha]_D^{25} +212°$ (c=0.1, ethanol).

PREPARATION 2

5-Amino-6,7-dichloro-2,3-dimethoxyquinoxaline

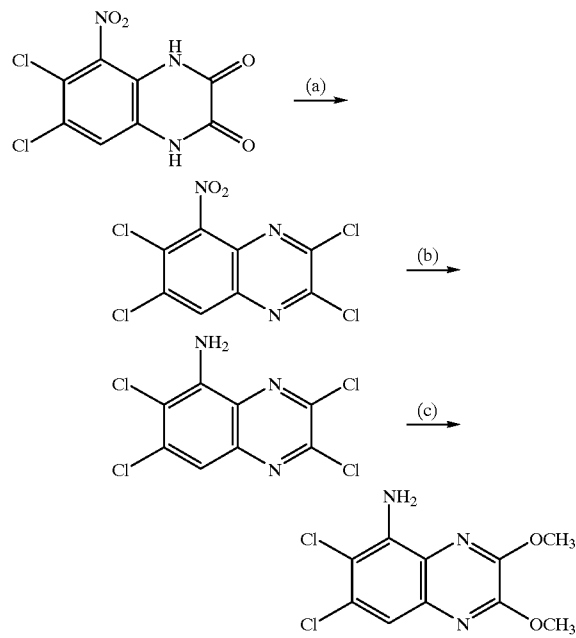

(a) A mixture of 6,7-dichloro-5-nitro-2,3(1H,4H)-quinoxalinedione (Example 1 of WO-A-94/00124, 84 g, 0.34 mol), thionyl chloride (840 ml) and dimethylformamide (0.5 ml) was heated under reflux for 3 hours, cooled and concentrated under reduced pressure. Ethyl acetate (300 ml) was added and removed by evaporation under reduced pressure and this procedure was then repeated with petroleum ether (bp 100–120° C). The solid residue was recrystallised from petroleum ether (bp 100–120° C.) to give 2,3,6,7-tetrachloro-5-nitroquinoxaline (78 g, 73%) as a light yellow solid.

H-NMR (300 MHz, $CDCl_3$): $\delta$=8.6 (1H, s).

(b) Tin(II) chloride dihydrate (346.3 g, 1.54 mol) was added to a solution of 2,3,6,7-tetrachloro-5-nitroquinoxaline (96.2 g, 0.31 mol) in ethyl acetate (1.8 liters). The mixture was heated under reflux for 4 hours, cooled and poured cautiously into an excess of aqueous saturated sodium bicarbonate solution. The mixture was filtered through CELITE (trade mark) filter aid washing well with ethyl acetate. The filter cake was macerated with further ethyl acetate and the solid material filtered off. The combined ethyl acetate phases were dried ($MgSO_4$) and concentrated under reduced pressure to give 5-amino-2,3,6,7-tetrachloroquinoxaline (73.4 g, 84%) as a yellow solid.

$^1$H NMR (300 MHz, $CDCl_3$): $\delta$=5.45 (2H, br, s), 7.47 (1H, s). m/z (thermospray): 385 ($MH^+$).

(In an alternative preparation, this reduction step was performed using iron filings in aqueous acetic acid).

(c) A solution of sodium methoxide (25% w/w solution in methanol, 274 ml, 1.28 mol) was added to a suspension of 5-amino-2,3,6,7-tetrachloroquinoxaline (72.4 g, 0.256 mol) in dry methanol (1 liter) and the resulting mixture was heated under reflux for 30 minutes. The mixture was cooled, concentrated under reduced pressure, and the residue partitioned between water and ethyl acetate (total of 8 liters). The organic extracts were dried ($MgSO_4$) and concentrated under reduced pressure. The crude product was triturated with methanol then dissolved in dichloromethane (2 liters) and filtered. The filtrate was concentrated under reduced pressure to give the title compound as a yellow solid (55.0 g, 79%).

$^1$H-NMR (300 MHz, $CDCl_3$): $\delta$=4.13 (3H, s), 4.14 (3H, s), 5.07 (2H, br s), 7.26 (1 H, s). m/z (thermospray): 274 ($MH^+$).

(In an alternative preparation, toluene was used as a co-solvent with methanol).

Solubility Data

The compounds of Examples 1 and 2 and Reference Example 1 were tested for their solubility in water and methanol at ambient temperature.

The results are shown in the Table below.

| Reference | Solubility in water at pH 7.3 (mg/ml) | Solubility in methanol (mg/ml) |
|---|---|---|
| Example 1 and 2 | >20 mg/ml | <1 mg/ml |
| Reference Example 1 | <1 mg/ml | ca. 15 mg/ml |

Lipophilicity Data

The lipophilicities of the compounds of Example 2 and Reference Example 1 were tested by the octanol/water partition method.

| Reference | log D |
|---|---|
| Example 2 | −1.7 |
| Reference Example 1 | −0.6 |

Pharmacological Data

The binding affinities for the glycine site of the NMDA receptor and the functional in vitro glycine antagonism of the compounds of Example 2 and Reference Example 1 were measured by the methods described on page 10.

The results were as follows:

| Binding affinity | |
|---|---|
| Example 2 | $IC_{50}$ = 2.4 nm |
| Reference Example 1 | $IC_{50}$ = 3.8 nm |
| Functional in vitro glycine antagonism | |
| Example 2 | $IC_{50}$ = 140 nm |
| Reference Example 1 | $IC_{50}$ = 190 nm |

What is claimed is:

1. A substantially pure compound of the formula:

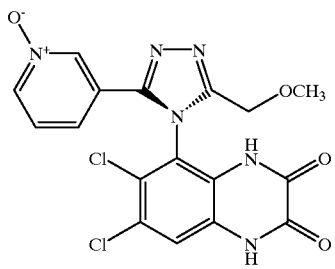
(I)

or a pharmaceutically acceptable salt thereof.

2. A compound as claimed in claim 1 that is at least of 90% w/w purity.

3. A compound as claimed in claim 2 that is at least of 95% w/w purity.

4. A compound as claimed in claim 3 that is at least of 98% w/w purity.

5. A compound as claimed in claim 1 wherein the pharmaceutically acceptable salt is a sodium salt.

6. A pharmaceutical composition comprising a compound of the formula (I), or a pharmaceutically acceptable salt or solvate thereof, as claimed in claim 1, together with a pharmaceutically acceptable diluent or carrier.

7. A compound of the formula:

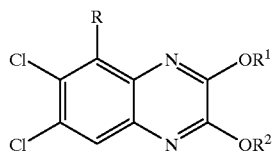
(II)

wherein R is group of the formula:

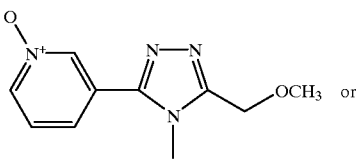
(III)

or

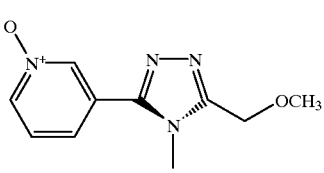
(IV)

and $R^1$ and $R^2$, either when taken alone or together, represent a group or groups that can be hydrolytically cleaved under acidic or basic conditions to provide the corresponding quinoxalinedione.

8. A compound of the formula (II) as claimed in claim 7 wherein $R^1$ and $R^2$ are either each independently selected from $C_1$–$C_4$ alkyl (preferably methyl or ethyl) and benzyl, optionally ring-substituted by from 1 to 3 substituents each independently selected from $C_1$–$C_4$ alkyl, $C_1$–$C_4$ alkoxy, halo, nitro and trifluoromethyl, or, when taken together, represent $C_1$–$C_6$ alkylene, CH(phenyl), CH(4-methoxyphenyl) or CH(3,4-dimethoxyphenyl).

9. A compound of the formula:

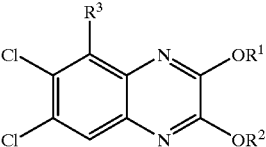
(VIII)

wherein $R^3$ is a group of the formula:

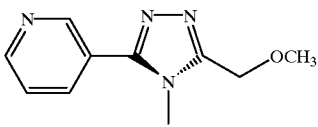
(X)

and $R^1$ and $R^2$ are either each independently selected from $C_1$–$C_4$ alkyl (preferably methyl or ethyl) and benzyl, optionally ring substituted by from 1 to 3 substituents each independently selected from $C_1$–$C_4$ alkyl, $C_1$–$C_4$ alkoxy, halo nitro and trifluoromethyl, or, when taken together, represent $C_1$–$C_6$ alkylene CH(phenyl), CH(4-methoxypenyl) or CH(3,4-dimiethoxyphenyl).

10. A process for the preparation of a compound of the formula (I), or a pharmaceutically acceptable salt thereof, as claimed in claim 1 comprising acidic or basic hydrolysis of a compound of the formula:

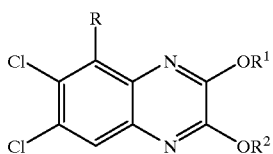

wherein R is group of the formula:

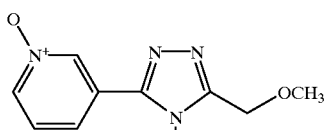

or

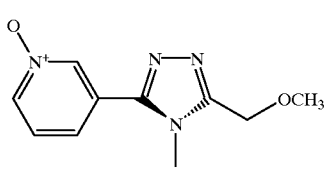

and $R^1$ and $R^2$, either when taken alone or together, represent a group or groups that can be hydrolytically cleaved under acidic or basic conditions to provide the corresponding quinoxalinedione, said process being followed by:

(i) when a compound of the formula (II) wherein R is a group of the formula (III) is used, separation of the atropisomer of the formula (I); and/or (ii) optionally, conversion of a compound of the formula (I) to a pharmaceutically acceptable salt thereof.

11. A process for the preparation of a compound of the formula (1), or a pharmaceutically acceptable salt thereof, as claimed in claim 1 comprising N-oxidation of a compound of the formula:

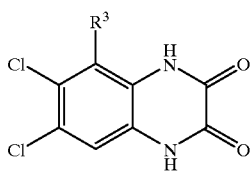

wherein $R^3$ is a group of the formula:

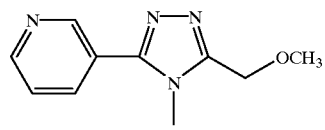

or

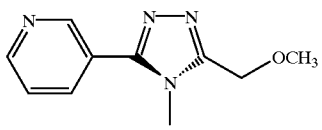

followed by work-up of the reaction under silica-free conditions, said process being followed by:

(i) when a compound of the formula (XI) wherein R is a group of the formula (IX) is used, separation of the atropisomer of the formula (1); and/or (ii) optionally, conversion of a compound of the formula (1) to a pharmaceutically acceptable salt thereof.

12. A process as claimed in claim 11 wherein the N-oxidation is carried out using potassium peroxy monosulfate in a reaction-inert solvent.

13. A compound of the formula (II) as claimed in claim 12 wherein $R^1$ and $R^2$ are either each independently selected from $C_1$–$C_4$ alkyl (preferably methyl or ethyl) and benzyl, optionally ring-substituted by from 1 to 3 substituents each independently selected from $C_1$–$C_4$ alkyl, $C_1$–$C_4$ alkoxy, halo, nitro and trifluoromethyl, or, when taken together, represent $C_1$–$C_6$ alkylene, CH(phenyl), CH(4-methoxyphenyl) or CH(3,4-dimethoxyphenyl).

14. A process for the preparation of a compound of the formula (1), or a pharmaceutically acceptable salt thereof, as claimed in claim 1 comprising acidic treatment of a silica complex of a compound of the formula (1), said process being optionally followed by conversion of a compound of the formula (1) to a pharmaceutically acceptable salt thereof.

15. A method of treating a disorder or condition by producing an antagonist effect at a NMDA receptor in a mammal comprising administering to said mammal an amount of a compound of Formula 1 or a pharmaceutically acceptable salt thereof as claimed in claim 1 that is effective in treating acute neurodegenerative diseases selected from the group consisting of stroke, transient ischemic attack, peri-operative ischaemia, global ischaemia following cardiac arrest, and traumatic head injury to the brain or spinal cord.

16. A method of treating a disorder or condition by producing an antagonist effect at a NMDA receptor in a mammal comprising administering to said mammal an amount of a compound of Formula 1 or a pharmaceutically acceptable salt thereof as claimed in claim 1 that is effective in treating epilepsy.

* * * * *